United States Patent [19]

Takamatsu et al.

[11] Patent Number: 4,968,800
[45] Date of Patent: Nov. 6, 1990

[54] NOVEL PLATINUM COMPLEX, ANTINEOPLASTIC AGENT CONTAINING THE SAME, AND INTERMEDIATE THEREFOR

[75] Inventors: Masanori Takamatsu, Toyonaka; Munetaka Matsui, Sakai; Yoshiaki Ikeda, Osaka, all of Japan

[73] Assignee: Kanebo Limited, Tokyo, Japan

[21] Appl. No.: 454,050

[22] Filed: Dec. 14, 1989

Related U.S. Application Data

[62] Division of Ser. No. 275,363, Nov. 23, 1988, Pat. No. 4,939,256.

[30] Foreign Application Priority Data

Feb. 4, 1988 [JP] Japan .................. 63-25463
Aug. 1, 1988 [JP] Japan .................. 63-192274

[51] Int. Cl.$^5$ .................. A61K 31/555; C07D 207/14; C07D 211/56
[52] U.S. Cl. .................. 546/11; 548/402
[58] Field of Search .................. 546/11; 548/402

[56] References Cited

U.S. PATENT DOCUMENTS 4,575,550 3/1986 Totani .................. 556/137

FOREIGN PATENT DOCUMENTS 176005 4/1986 European Pat. Off. .
273315 7/1988 European Pat. Off. .......... 546/11

Primary Examiner—Mark L. Berch
Attorney, Agent, or Firm—Wegner & Bretschneider

[57] ABSTRACT

A platinum complex of the formula

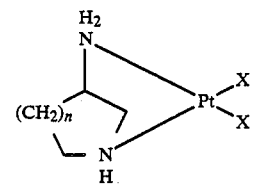

wherein n is 1 or 2 and X is chlorine, bromine or iodine is described, which is useful intermediate; thus, it can be reacted with silver nitrate or silver sulfate and the resulting compound can be treated with an anion exchange resin or barium hyroxide to give a compound of the formula

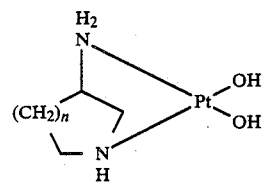

which can then be reacted with glycolic acid to furnish a compound of the formula

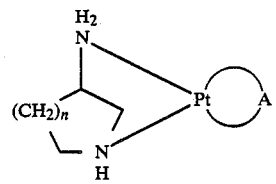

wherein n is 1 or 2 and A is —OCOCH$_2$O—; these products are useful antineoplastic agents.

1 Claim, No Drawings

NOVEL PLATINUM COMPLEX, ANTINEOPLASTIC AGENT CONTAINING THE SAME, AND INTERMEDIATE THEREFOR

This application is a divisional application of U.S. Ser. No. 275,363 filed Nov. 23, 1988, U.S. Pat. No. 4,939,256.

This invention relates to a novel platinum complex, an antineoplastic agent containing the compound, and an intermediate for preparing the active compound. More particularly, it relates to a platinum complex of the formula:

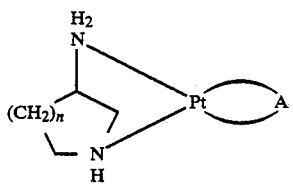

wherein n is an integer of 1 or 2 and A is a ligand of the formula:

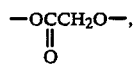

an antineoplastic agent containing the compound as an active ingredient, and an intermediate for preparing the active platinum complex.

PRIOR ART

It is known that cisplatin [chemical name: cis-diamminedichloroplatinum (II)] of the formula:

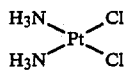

has excellent antineoplastic activity and hence is useful as an antineoplastic agent, and this compound has been clinically used. However, this compound has high toxicity, particularly high side effects on kidney which becomes the dose limiting factor [cf. The American Journal of Medicine, 65, 307–314]. Accordingly, it has been desired to develop other platinum complex having excellent antineoplastic activity with less nephrotoxicity.

BRIEF DESCRIPTION OF THE INVENTION

The present inventors have intensively studied to find a novel platinum complex which has excellent antineoplastic activity and less toxicity than the known cisplatin and have found that the novel platinum complex of the above formula [I] has the desired properties.

An object of the invention is to provide a novel platinum complex having excellent antineoplastic activity with less toxicity. Another object of the invention is to provide a pharmaceutical composition useful as an antineoplastic agent for the treatment of tumors which comprises as an active ingredient the platinum complex in admixture with a pharmaceutically acceptable carrier or diluent. A further object of the invention is to provide an intermediate useful for preparing the active platinum complex. These and other objects and advantages of the invention will be apparent to those skilled in the art from the following description.

DETAILED DESCRIPTION OF THE INVENTION

The novel platinum complex of the invention has the formula [I] as set forth hereinabove, which includes a glycolato-3-aminopyrrolidine platinum (II) (when n is 1) and a glycolato-3-aminopiperidine platinum (II) (when n is 2).

The platinum complex [I] of this invention includes a pair of stereoisomers due to the orientation of the ligand A of the formula:

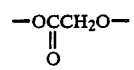

(hereinafter, the ligand is referred to as "glycolato group", and the stereoisomers are referred to as "geometrical isomers"), and further, the compound [I] includes a pair of stereoisomers due to the configuration of the amino group on the cyclic amine of the formula:

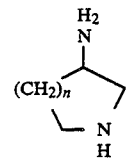

wherein n is as defined above (hereinafter, the stereoisomers are referred to as "optical isomers"). This invention includes these isomers and a mixture thereof.

In the present specification, these isomers are expressed as follows.

Among the pair of geometrical isomers, the geometical isomer which has a peak due to the carbonyl of the glycolato group at the low magnetic field in $^{13}$C-NMR spectrum (solvent for measurement, D$_2$O) is expressed by referring to a symbol "α", and the geometrical isomer which has the peak at the high magnetic field is expressed by referring to a symbol "β". Besides, the configuration of the amino group on the ring of the cyclic amine [II] is expressed by the symbols of "R", "S" or "RS". Thus, for example, in case of the glycolato-3-aminopyrrolidine platinum (II), when the stereoisomer shows a peak due to the carbonyl in the glycolato group at the low magnetic field and is coordinated with (3R)-3-aminopyrrolidine, it is expressed as "α-glycolato-(3R)-3-aminopyrrolidine platinum (II)". Other stereoisomers are expressed likewise.

In accordance with the above expression manner, the stereoisomers of glycolato-3-aminopyrrolidine platinum (II) of this invention are listed as follows.

α-Glycolato-(3RS)-3-aminopyrrolidine platinum (II)
β-Glycolato-(3RS)-3-aminopyrrolidine platinum (II)
α-Glycolato-(3R)-3-aminopyrrolidine platinum (II)
β-Glycolato-(3R)-3-aminopyrrolidine platinum (II)
α-Glycolato-(3S)-3-aminopyrrolidine platinum (II)
β-Glycolato-(3S)-3-aminopyrrolidine platinum (II)

The stereoisomers of glycolato-3-aminopiperidine platinum (II) are listed as follows.

α-Glycolato-(3RS)-3-aminopiperidine platinum (II)
β-Glycolato-(3RS)-3-aminopiperidine platinum (II)
α-Glycolato-(3R)-3-aminopiperidine platinum (II)

β-Glycolato-(3R)-3-aminopiperidine platinum (II)
α-Glycolato-(3S)-3-aminopiperidine platinum (II)
β-Glycolato-(3S)-3-aminopiperidine platinum (II)

The platinum complex [I] -of this invention can be prepared, for example, by the following two process (Process A and Process B).

PROCESS A

The Process A is illustrated by the following reaction scheme:

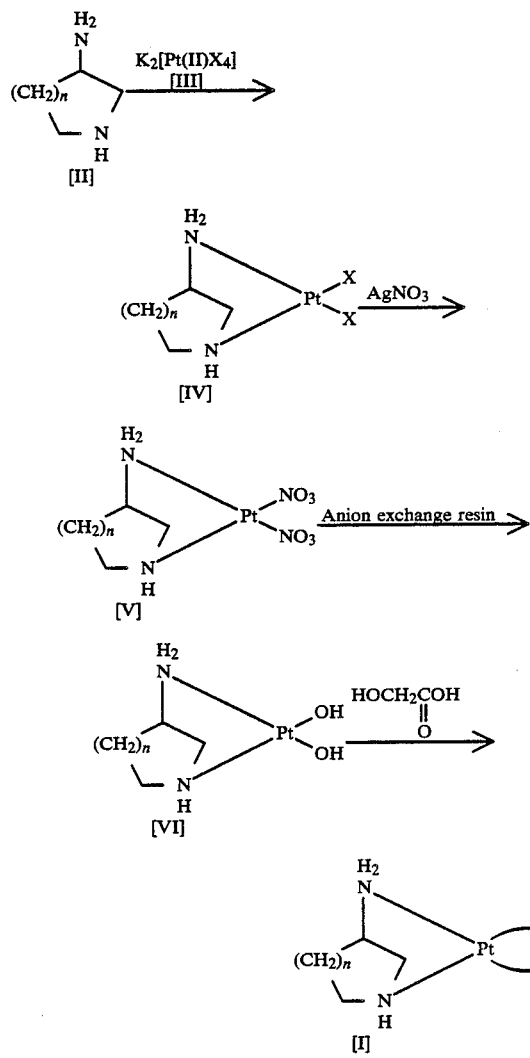

wherein X is chlorine, bromine or iodine atom, and n and A are as defined above.

The cyclic amine [II] and the compound [III] are usually reacted in a solvent of water at a temperature of from room temperature to 100° C. for 5 to 50 hours to give a novel halogenoplatinum complex [IV]. The compound [II] is usually used in an amount of 1 to 1.5 mole to 1 mole of the compound [III].

The halogenoplatinum complex [IV] is reacted with silver nitrate to give the compound [V]. This reaction is usually carried out in water as a solvent at room temperature for 1 to 4 days under light screening. Silver nitrate is used in an amount of 1.8–2.5 moles, preferably 2.0–2.2 moles, to 1 mole of the compound [IV]. After completion of the reaction, an aqueous potassium chloride solution is added to the reaction mixture in order to precipitate and remove excess silver nitrate in the form of silver chloride to give an aqueous solution of the compound [V]. The compound [V] thus obtained is usually used in the subsequent reaction without isolation.

The aqueous solution of the compound [V] obtained above is then treated with an anion exchange resin (OH type) to give an aqueous solution of the compound [VI], which is reacted with glycolic acid to give the desired platinum complex [I] of this invention. The treatment with an anion exchange resin is usually carried out, for example, by passing the aqueous solution of the compound [V] through a column packed with AMBERLITE ® IRA-400 (OH type) (manufactured by Rohm and Haas and sold by Organo). The reaction of the compound [VI] and glycolic acid is usually carried out by adding glycolic acid to an aqueous solution of the compound [VI] and stirring the mixture at a temperature of from room temperature to 100° C., preferably from 50° to 70° C., for 3 to 10 hours. Glycolic acid is usually used in an amount of 0.9–1.1 mole to 1 mole of the compound [IV] which is used for the preparation of the aqueous solution of the compound [VI].

PROCESS B

The Process B is illustrated by the following reaction scheme:

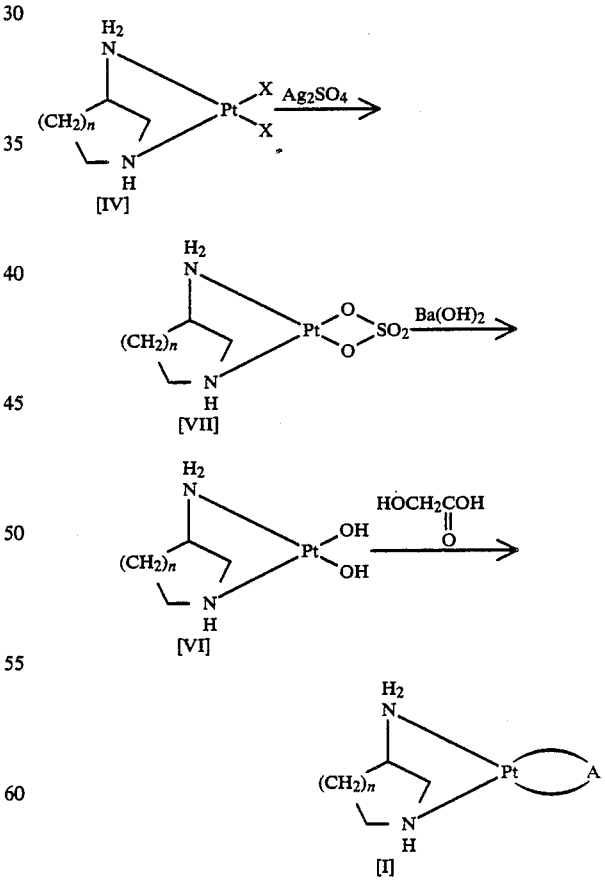

wherein X, n and A are as defined above.

The compound [IV] is reacted with silver sulfate to give the compound [VII]. This reaction is usually carried out in water as a solvent at room temperature for 1 to 4 days under light screening. Silver sulfate is usually used in an amount of 0.8–1.3 mole, preferably 1.0–1.1 mole, to 1 mole of the compound [IV]. After completion of the reaction, an aqueous potassium chloride solution is added to the reaction mixture to precipitate and remove excess silver sulfate in the form of silver chloride to give an aqueous solution of the compound [VII]. The compound [VII] is used in the subsequent reaction without isolation.

The aqueous solution of the compound [VII] is then reacted with barium hydroxide to give the compound [VI]. This reaction is usually carried out at room temperature for 1 to 3 days. Barium hydroxide is usually used in an amount of 0.9–1.5 mole to 1 mole of the compound [IV] which is used for the preparation of the compound [VII]. After completion of the reaction, the precipitated barium sulfate is removed by filtration to give an aqueous solution of the compound [VI]. The compound [VI] is reacted with glycolic acid in the same manner as in Process A to give the desired platinum complex [I] of the invention.

The platinum complex [I] prepared by the above processes can be purified by conventional purification methods, such as column chromatography and/or recrystallization.

The platinum complex [I] of the invention as prepared by the above processes is usually a mixture of a pair of geometric isomers due to the orientation of the glycolato group, but when the reaction product is recrystallized from a mixed solvent of methanol-water, there can be isolated a geometric isomer which has a lower solubility in water. The geometric isomer can also be obtained from the mother liquor in the above recrystallization in the following manner. That is, when the geometric isomers are dissolved in water and heated at a temperature of, for example, 45°–50° C., for 8 to 9 hours, the isomers are mutually isomerized to give a mixture of the isomers of about 1:1, and hence, the geometric isomer having a lower solubility in water is isolated by distilling off the solvent of mother liquor in the recrystallization, dissolving the residue in water, heating the solution, and the recrystallizing from a mixed solvent of methanol-water.

On the other hand, when the above mother liquor in recrystallization is concentrated to dryness, there can be obtained a platinum complex comprising mainly a geometric isomer having a higher solubility in water.

The optically active platinum complex of the invention can be prepared by using an optically active cyclic amine [II] or a salt thereof in the above processes. The starting optically active cyclic amine [II] can be prepared by subjecting a racemic mixture thereof to resolution by forming a salt with an optically active organic acid (e.g. optically active tartaric acid), or alternatively may be prepared by reducing an optically active aminolactam of the formula:

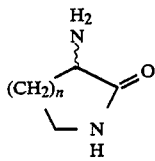

[VIII]

wherein n is as defined above, or a salt thereof.

The platinum complex [I] of this invention is useful as an antineoplastic agent for the treatment of various malignant tumors, for example, lung cancer, gastric cancer, breast cancer, testicular tumor, bladder cancer, ovarian tumor, head and neck tumors, osteosarcoma, and the like.

The platinum complex [I] of this invention is administered parenterally in the dosage form such as injections or suppositories, preferably injections. The injection preparation containing the platinum complex [I] of this invention may be prepared by a conventional method, for example, by dissolving the compound in purified water and adding thereto an isotonicity (e.g. mannitol, sodium chloride, glucose, sorbitol, glycerol, xylitol, fructose, maltose, mannose, etc.), and optionally a stabilizer and a preservative. The preparation may be in the form of a lyophilized product which is dissolved in a solvent for injection when used.

The dose of the platinum complex [I] of this invention may vary depending on age, body surface of patients and severity of the diseases, but is usually in the range of 20 to 2,000 mg/$m^2$ (area of body surface), preferably 50 to 1,500 mg/$m^2$ (area of body surface) per one time, which is usually administered once a day. The compound may be administered continuously for the days to be treated but if necessary, the administration may rest intermittently on some days.

The platinum complex [I] of this invention shows excellent antineoplastic activity. For instance, in an experiment of antineoplastic activity in tumor bearing mice, the platinum complex [I] showed excellent increase in life span in an optimal dose like the known cisplatin (cf. Experiment 1 shown hereinafter). Moreover, the platinum complex [I] was effective on cisplatin-resistant tumor cells (cf. Experiment 2 shown hereinafter).

On the other hand, the platinum complex [I] shows less side effect on kidney than cisplatin. For instance, in the test using blood urea nitrogen value (BUN value) as an index, the platinum complex [I] of this invention showed lower nephrotoxicity in comparison with cisplatin [cf. Experiment 3 shown hereinafter).

Moreover, the platinum complex [I] of this invention showed a lower lethal toxicity than cisplatin (cf. Experiment 4 shown hereinafter).

Besides, the platinum complex [I] of this invention has better solubility in water than cisplatin and hence is more easily prepared in the pharmaceutical preparations.

Thus, the platinum complex [I] of this invention can be used as an excellent antineoplastic agent.

The activities of the platinum complex [I] of this invention are illustrated by the following experiments.

EXPERIMENT 1

Test of antitumor activity (1) Test materials:

(a) Animals: $BDF_1$ male mice (6 week age, weighing 22 to 25 g, 4 animals per each group)

(b) Tumor cells: Leukemia P388

(c) Test compounds:

1. Platinum complex A-1 (compound of this invention): a mixture of α-glycolato-(3RS)-3-aminopyrrolidine platinum (II) (Isomer a-1) and β-glycolato-(3RS)-3-aminopyrrolidine platinum (II) (Isomer a-2) (about 1:1 by weight) (the product in Example 1)

2. Platinum complex A-2 (compound of this invention): α-glycolato-(3RS)-3-aminopyrrolidine platinum (II) (Isomer a-1) (the product in Example 2)

3. Platinum complex A-3 (compound of this invention): a mixture of α-glycolato-(3RS)-3-aminopyrrolidine platinum (II) (Isomer a-1) and β-glycolato-(3RS)-3-aminopyrrolidine platinum (II) (Isomer a-2) (about 2:8 by weight) (the product in Example 2)

4. Platinum complex B-1 (compound of this invention): a mixture of α-glycolato-(3RS)-3-aminopiperidine platinum (II) (Isomer b-1) and β-glycolato-(3RS)-3-aminopiperidine platinum (II) (Isomer b-2) (about 6:4 by weight) (the product in Example 5)

5. Cisplatin (reference compound)

(2) Test method:

Tumor cells ($1 \times 10^6$ per mouse) were intraperitoneally inoculated into mice. After 24 hours, a solution of each test compound in physiological saline solution was intraperitoneally administered to the mice. In control mice, only physiological saline solution was intraperitoneally administered.

Survival days of the mice was observed until 30th day after the inoculation of tumor cells. Mean survival days (X) in the mice administered with test compound and mean survival days (Y) in the control mice were measured and the increase in life span (ILS %) was calculated by the following equation:

$$\text{Increase in life span } (ILS\ \%) = \frac{X - Y}{Y} \times 100$$

(3) Test results:
The results are shown in Table 1.

TABLE 1

| Test compound | Dose (mg/kg) | Increase in life span (ILS %) |
|---|---|---|
| Platinum complex A-1 | 25 | 74 |
| | 50 | 167 |
| | 100 | −43 |
| Platinum complex A-2 | 25 | 108 |
| | 50 | 172 |
| | 100 | 115 |
| Platinum complex A-3 | 25 | 111 |
| | 50 | 170 |
| | 100 | 26 |
| Platinum complex B-1 | 25 | 131 |
| | 50 | 174 |
| | 100 | −45 |
| Cisplatin | 5 | 108 |
| | 10 | 167 |
| | 20 | −11 |

As is clear from the above test results, the platinum complex of this invention showed excellent increase of life span as like as cisplatin.

EXPERIMENT 2

Effects on cisplatin-resistant tumor cells (1) Test materials:
(a) Tumor cells:
1. L1210 cells
2. Cisplatin-resistant L1210 cells (hereinafter, referred to as L1210/DDP), which is available from Cancer Chemotherapy Center, Japanese Foundation for Cancer Research
(b) Test compounds:
The same as in Experiment 1.
(c) Cultivation medium:
RPMI-1640 medium containing 10% (v/v) fetal bovine serum, which was prepared as follows:
RPMI-1640 (manufactured by GIBCO) (10.4 g), sodium hydrogen carbonate (1.3 g), streptomycin sulfate (100 g), penicillin G potassium (63.5 g) and a 1% aqueous solution of β-mercaptoethanol (40 μ) were dissolved in distilled water (one liter). To this mixture (90 parts by volume) was added fetal bovine serum (manufactured by GIBCO) (10 parts by volume) to give RPMI-1640 medium containing 10% (v/v) fetal bovine serum (hereinafter, referred to as "serum-containing RPMI-1640 medium").

(2) Test method:

L1210 cells or L1210/DDP cells were added to the serum-containing RPMI-1640 medium to prepare a cell suspension ($3 \times 10^5$ cells/ml). The cell suspension (each 1 ml) was seeded onto a microplate (Falcon 3047, manufactured by Falcon) and cultivated in air containing 5% $CO_2$ gas at 37° C. (one group, 3 wells). After cultivating of 24 hours, a solution of each test compound (1 ml) (which was prepared by dissolving each test compound in the serum-containing RPMI-1640 medium in various concentrations) was added to the medium, and the mixture was cultivated under the same conditions for 48 hours. After the cultivation, the number of viable cells was counted by Trypan Blue exclusion test method, and the mean number of viable cells in each group was calculated. Besides, in the control group, the above was repeated by using the serum-containing RPMI-1640 medium instead of the solution of test compound, and the mean number of viable cells in the control group was calculated likewise. From the mean number of viable cells in various concentration of test compound and the mean number of viable cells in the control group, the concentration required for 50% inhibition of growth ($IC_{50}$) was calculated by probit method. Then, the resistance index of test compound was calculated by the following equation:

$$\text{Resistance index} = \frac{IC_{50} \text{ to } L1210/DDP}{IC_{50} \text{ to } L1210}$$

The above test was repeated for 2 to 4 times, and the mean resistance index was obtained.

(3) Test results:
The results are shown in Table 2.

TABLE 2

| Test compound | Times of test | Resistance index Mean (minimum, maximum) |
|---|---|---|
| Platinum complex A-1 | 2 | 4.8 (4.2, 5.4) |
| Platinum complex A-2 | 4 | 4.5 (3.1, 5.6) |
| Platinum complex A-3 | 2 | 4.6 (4.6, 4.6) |
| Platinum complex B-1 | 2 | 4.3 (3.2, 5.4) |
| Cisplatin | 4 | 15.1 (11.8, 17.2) |

As is clear from the above test results, the platinum complex of this invention showed lower resistance index to cisplatin-resistant tumor cells and hence is also effective on cisplatin-resistant tumor cells.

EXPERIMENT 3

Side effect on kidney

It was studied in the blood urea nitrogen value (BUN value) as an index.

(1) Test materials:
(a) Animal: $BDF_1$ male mice (6 week age, weighing 22–25 g, 5 animals per each group)
(b) Test compounds:
The same as in Experiment 1.
The dose of each test compound was the same as the dose showing maximum increase in life span in Experiment 1 (i.e. the doses of Platinum complex A-1, Platinum complex A-2, Platinum complex A-3 and Platinum complex B-1 were 50 mg/kg respectively, and the dose of cisplatin was 10 mg/kg) and 1.5 times higher dose thereof.

(2) Test method:

Each test compound was dissolved in a physiological saline solution, and the solution (0.1 ml/10 g body weight) was intraperitoneally administered. In the control mice only the physiological saline solution (0.1 ml/10 g body weight) was intraperitoneally administered. On the 4th day after the administration, the test compound-administered mice and the control mice were bleeded from the femoral artery, and the collected blood was centrifuged at 3,000 r.p.m. at 4° C. for 15 minutes to give a test serum. BUN value in the test serum was measured by a urease indophenol method using a kit for measuring urea nitrogen (Urea NB-Test Wako, manufactured by Wako Pure Chemical Industries, Ltd.). That is, the above test serum (20 μl) was taken in a test tube and thereto was added color reagent A [a mixture of a urease solution (one part by volume) and phosphate buffer (pH 7.0, 20 parts by volume), 2.0 ml], and the mixture was mixed well and incubated at 37° C. for 15 minutes. To the reaction mixture was added color reagent B [a solution containing sodium hypochlorite and sodium hydroxide, 2.0 ml], and the mixture was mixed well and incubated at 37° C. for 10 minutes to give a test solution.

Separately, an aqueous solution containing urea (50 mg/dl) and distilled water were each taken in test tubes (each 20 μl), and these were treated with color reagent A and color reagent B in the same manner as described above to give a standard solution and a blank solution, respectively.

The absorbance of the standard solution and test solution was measured at 570 nm with a spectrophotometer with reference to the blank solution as a control, and BUN value in the test serum was calculated by the following equation:

$$BUN \text{ value (mg/dl)} = \frac{\text{Absorbance of test solution}}{\text{Absorbance of standard solution}} \times 50$$

In accordance with the above method, BUN value in serum of the control mice (BUNc) and BUN value in serum of the mice administered with test compound (BUNt) were measured, and the rate of change of BUN value was calculated by the following equation, and the mean value in each test compound-administered group was determined.

$$\text{Rate of change of } BUN \text{ value} = \frac{BUNt - BUNc}{BUNc} \times 100$$

(3) Test results:
The results are shown in Table 3.

TABLE 3

| Test compound | Dose (mg/kg) | Rate of change of BUN value (%) |
|---|---|---|
| Platinum complex A-1 | 50 | +5 |
|  | 75 | −36 |
| Platinum complex A-2 | 50 | −23 |
|  | 75 | −33 |
| Platinum complex A-3 | 50 | −17 |
|  | 75 | −19 |
| Platinum complex B-1 | 50 | −34 |
|  | 75 | −17 |
| Cisplatin | 10 | +106 |

TABLE 3-continued

| Test compound | Dose (mg/kg) | Rate of change of BUN value (%) |
|---|---|---|
|  | 15 | +128 |

As is clear from the above test results, the platinum complex of this invention did not increase BUN value which means that the compound shows less side effect on kidney.

EXPERIMENT 4

Acute toxicity ($LD_{50}$)

(1) Test materials:
(a) Animal: $BDF_1$ male mice (6 week age, weighing 22–25 g, 5 animals per each group)
(b) Test compound:
The same as in Experiment 1.

(2) Test method:

Each test compound was dissolved or suspended in a physiological saline solution, and the solution or suspension (0.1 ml/10 g body weight) was intraperitoneally administered to mice. The number of mice that died was counted until 14th day after administration of test compound, and the acute toxicity ($LD_{50}$) was calculated by Weil method.

(3) Test results:
The results are shown in Table 4.

TABLE 4

| Test compound | $LD_{50}$ (mg/kg) |
|---|---|
| Platinum conplex A-1 | 112.8 |
| Platinum complex A-2 | 112.8 |
| Platinum complex A-3 | 107.0 |
| Platinum complex B-1 | 57.0 |
| Cisplatin | 14.8 |

As is shown in the above results, the platinum complex of this invention showed lower toxicity than cisplatin.

The compounds and preparations of this invention are illustrated by the following Examples and Reference Examples but this invention should not be construed to be limited thereto. The chemical shift δ(ppm) in $^1H$-NMR spectrum and $^{13}C$-NMR spectrum was measured by using heavy water ($D_2O$) as a solvent and sodium 2,2-dimethyl-2-silapentane-5-sulfonate as the internal standard at 300 MHz.

EXAMPLE 1

Preparation of glycolato-3-aminopyrrolidine platinum (II) [a mixture of α-glycolato-(3RS)-3-aminopyrrolidine platinum (II) (Isomer a-1) and β-glycolato-(3RS)-3-aminopyrrolidine platinum (II) (Isomer a-2) in about 1:1 by weight (Platinum complex A-1 of this invention)], by Process A:

(1) Cis-dichloro-(3RS)-3-aminopyrrolidine platinum (II):

To a solution of platinum (II) potassium chloride (12.2 g) in water (800 ml) is added (3RS)-3-aminopyrrolidine (2.5 g), and the mixture is stirred at room temperature for 19 hours. The precipitated solid is removed by filtration, and the filtrate is concentrated under reduced pressure. To the residue is added a small amount of water, and the resulting crystals are separated by filtration and washed with water and acetone to give cis-dichloro-(3RS)-3-aminopyrrolidine platinum (II) (6.9 g) as pale yellow crystal.

m.p. 200°–215° C. (decomp. with coloring)
Elementary analysis for $C_4H_{10}Cl_2N_2Pt$:
Calcd. (%): C,13.64; H,2.86; N,7.96.
Found (%): C,13.58; H,2.80; N,8.00.

(2) Glycolato-3-aminopyrrolidine platinum (II):

The above cis-dichloro-(3RS)-3-aminopyrrolidine platinum (II) (3.0 g) is suspended in water (50 ml), and to the suspension is added silver nitrate (2.89 g). The mixture is stirred at room temperature for 2 days under light screening, and the insoluble materials are filtered off. To the filtrate is added a 0.5% aqueous potassium chloride solution until no turbidity appears. Excess silver nitrate is precipitated in the form of silver chloride and removed by filtration to give an aqueous solution of cis-dinitrato-(3RS)-3-aminopyrrolidine platinum (II). The aqueous solution is passed through a column packed with AMBERLITE ® IRA-400 (manufactured by Rohm and Haas and sold by Organon) (OH type) (50 ml) to give an aqueous solution of cis-dihydroxo-(3RS)-3-aminopyrrolidine platinum (II). the aqueous solution is added glycolic acid (648 mg), and the mixture is stirred at 60–70° C. for 6 hours. The reaction mixture is concentrated under reduced pressure, and the residue is purified by silica gel column chromatography [developer: methanol-water (10:1)]. The eluate is monitored by thin layer chromatography [thin layer plate: Kieselgel 60F$_{254}$, manufactured by Merck & Co., developer: methanol-water (10:1)] and thereby the fractions containing a compound of Rf 0.20 are collected. The solvent is distilled off under reduced pressure, and to the residue is added a small amount of methanol, and the resulting crystals are separated by filtration to give a mixture of stereoisomers of glycolato-3-aminopyrrolidine platinum (II) (814 mg) as colorless crystal. It is confirmed by $^1$H-NMR and $^{13}$C-NMR that it is a mixture of α-glycolato-(3RS)-3-aminopyrrolidine platinum (II) (Isomer a-1) and β-glycolato-(3RS)-3-aminopyrrolidine platinum (II) (Isomer a-2) (about 1:1 by weight). The isomer mixture has the following physical properties.

m.p.: It is gradually colored in gray at 155°–165° C. and becomes black and is decomposed at around 197° C.

IR (KBr) cm$^{-1}$: 3428, 3152, 2984, 2888, 2812, 1668, 1628, 1598, 1376, 1340, 1298, 1066

SIMS (Secondary ion mass spectrum) m/z: 356 [(M+H)$^+$ based on $^{195}$Pt]

$^1$H-NMR (D$_2$O) δ: 1.88–2.07 (2H, m, peak based on Isomer a-1 and Isomer a-2), 2.39 (0.5H, dd, peak based on Isomer a-2), 2.43 (0.5H, dd, peak based on Isomer a-1), 3.05 (0.5H, d, peak based on Isomer a-1), 3.08 (0.5H, d, peak based on Isomer a-2), 3.17–3.34 (2H, m, peak based on Isomer a-1 and Isomer a-2), 3.70–3.80 (1H, m, peak based on Isomer a-1 and Isomer a-2), 3.98 (1H, s, peak based on Isomer a-1), 4.04 (1H, s, peak based on Isomer a-2)

$^{13}$C-NMR (D$_2$O) δ: 30.25, 52.97, 56.68, 62.98, 69.50 197.06 (all of these, six peaks based on Isomer a-1), 30.20, 53.45, 56.05, 63.74, 69.70, 196.93 (all of these, six peaks based on Isomer a-2)

Elementary analysis for $C_6H_{12}N_2O_3Pt$:
Calcd. (%): C,20.29; H,3.40; N,7.89.
Found (%) ; C,20.27; H,3.34; N,7.71.

EXAMPLE 2

Preparation of glycolato-3-aminopyrrolidine platinum (II) [α-glycolato-(3RS)-3-aminopyrrolidine platinum (II) (Isomer a-1, Platinum complex A-2 of this invention), and a mixture of α-glycolato-(3RS)-3-aminopyrrolidine platinum (II) (Isomer a-1) and β-glycolato-(3RS)-3-aminopyrrolidine platinum (II) (Isomer a-2) in about 2:8 by weight (Platinum complex A-3 of this invention)], by Process B:

Cis-dichloro-(3RS)-3-aminopyrrolidine platinum (II) [40.3 g, prepared in the same manner as described in Example 1-(1)] is suspended in water (400 ml), and to the suspension is added silver sulfate (35.7 g). The mixture is stirred at room temperature for 4 days under light screening, and the insoluble materials are filtered off. To the filtrate is added a 0.5% aqueous potassium chloride solution until no turbidity appears. Excess silver sulfate is precipitated in the form of silver chloride and removed by filtration to give an aqueous solution of cis-sulfato-(3RS)-3-aminopyrrolidine platinum (II). To the aqueous solution is added barium hydroxide·8 hydrate (36.1 g), and the mixture is stirred ar toom temperature for 2 days. The precipitated barium sulfate and other insoluble materials are removed by filtration to give an aqueous solution of cis-dihydroxo-(3RS)-3-aminopyrrolidine platinum (II). To the aqueous solution is added glycolic acid (8.7 g), and the mixture is stirred at 60°–70° C. for 6 hours. The reaction mixture is concentrated under reduced pressure, and to the residue is added methanol (200 ml) to give crude glycolato-3-aminopyrrolidine platinum (II) [a mixture of α-glycolato(3RS)-3-aminopyrrolidine platinum (II) (Isomer a-1) and β-glycolato-(3RS)-3-aminopyrrolidine platinum (II) (Isomer a2)]. The product is recrystallized from a mixed solvent of methanol-water (10:1) to give α-glycolato-(3RS)-3-aminopyrrolidine platinum (II) (Isomer a-1) (6.1 g) as colorless crystal. This compound has the following physical properties.

m.p.: It starts to color in gray at around 192° C. and becomes black and is decomposed at around 207° C.

Rf value: about 0.20 [thin layer plate, Kieselgel 60F254 (manufactured by Merck & Co., developer: methanol-water (10:1)]

IR (KBr) cm$^{-1}$: 3448, 3128, 2992, 2880, 2812, 1668, 1340, 1298

SIMS (Secondary ion mass spectrum) m/z: 356 [(M+H)$^+$ based on $^{195}$Pt]

$^1$H-NMR (D$_2$O) δ: 1.88–2.07 (2H, m), 2.43 (1H, dd, J=10 Hz, 1 Hz), 3.05 (1H, d, J=10 Hz), 3.18 (1H, d, J=4 Hz), 3.21–3.34 (1H, m), 3.71–3.80 (1H, m), 3.98 (2H, s)

$^{13}$C-NMR (D$_2$O) δ: 30.25, 52.97, 56.68, 62.98, 69.50, 197.06

Elementary analysis for $C_6H_{12}N_2O_3Pt$:
Calcd. (%): C,20.29; H,3.40; N,7.89.
Found (%): C,20.26; H,3.32; N,7.82.

The mother liquor in the above recrystallization for obtaining Isomer a-1 is concentrated under reduced pressure to give residue (7.9 g). The residue (1.2 g) is dissolved in water (4 ml) and the solution is stirred at 45°–50° C. for 9 hours. To the mixture is added methanol (80 ml), and the mixture is allowed to stand at 0°–2° C. overnight. The precipitated crystals are separated by filtration to give Isomer a-1 (435 mg). The filtrate is stirred at 65° C. for 6 hours and then allowed to stand at 0°–2° C. for 2 days, and the precipitates are separated by filtration to give crystals (220 mg) which are mainly of Isomer a-1. The filtrate is concentrated to under reduced pressure, and the residue is washed with methanol (3 ml) to give a mixture (200 mg) of Isomer a-1 and Isomer a-2 (about 2:8). The isomer mixture has the following physical properties.

m.p.: It starts to color in gray at around 193° C. and becomes black and is decomposed at around 208° C.

IR (KBr) cm¹: 3440, 3156, 2964, 2880, 2808, 1668, 1336, 1286

SIMS (Secondary ion mass spectrum) m/z: 356 [(M+H)+ based on $^{195}$Pt]

$^1$H-NMR (D$_2$O) δ: 1.88–2.07 (2H, m, peak based on Isomer a-1 and Isomer a-2), 2.39 (0.8H, dd, peak based on Isomer a-2), 2.43 (0.2H, dd, peak based on Isomer a-1), 3.05 (0.2H, d, peak based on Isomer a-1), 3.08 (0.8H, d, peak based on Isomer a-2), 3.17–3.34 (2H, m, peak based on Isomer a-1 and Isomer a-2), 3.70–3.80 (1H, m, peak based on Isomer a-1 and Isomer a-2), 3.98 (0.4H, s, peak based on Isomer a-1), 4.04 (1.6H, s, peak based on Isomer a-2)

$^{13}$C-NMR (D$_2$O) δ: 30.25, 52.97, 56.68, 62.98, 69.50, 197.06 (all of these, six peaks based on Isomer a-1), 30.20, 53.45, 56.05, 63.74, 69.70, 196.93 (all of these, six peaks based on Isomer a-2)

Elementary analysis for C$_6$H$_{12}$N$_2$O$_3$Pt:
Calcd. (%): C,20.29; H,3.40; N,7.89.
Found (%): C,20.19; H,3.24; N,7.98.

EXAMPLE 3

Preparation of optically active glycolato-3-aminopyrrolidine platinum (II) [α-glycolato-(3R)-3-amino-pyrrolidine platinum (II) (Isomer a-3, Platinum complex A-4 of this invention], by Process B:

(1-A) Cis-dichloro-(3R)-3-aminopyrrolidine platinum (II):

(3R)-3-Aminopyrrolidine D(−)-tartrate (236 mg) prepared in Reference Example 1-(1) is dissolved in water (40 ml) and thereto is added sodium hydroxide (80 mg), and the mixture is stirred at room temperature. To the solution is added platinum (II) potassium chloride (415 mg), and the mixture is stirred at room temperature overnight. The precipitated solid is removed by filtration, and the filtrate is concentrated under reduced pressure. To the residue is added water (2 ml), and the resulting crystals are separated by filtration and washed with water and acetone to give cis-dichloro-(3R)-3-aminopyrrolidine platinum (II) (200 mg) as pale yellow crystal.

m.p.: It is gradually colored in gray at around 180° C. and becomes black and is decomposed at around 210°–215° C.

$[\alpha]_D^{20}$ +15.8° (c=0.4, H$_2$O)

Elementary analysis for C$_4$H$_{10}$Cl$_2$N$_2$Pt:
Calcd. (%): C,13.64; H,2.86; N,7.96.
Found (%): C,13.63; H,2.65; N,7.95.

(1-B) Cis-dichloro-(3R)-3-aminopyrrolidine platinum (II):

(3R)-3-Aminopyrrolidine (400 mg) prepared in Reference Example 1-(3) is dissolved in water (200 ml) and thereto is added platinum (II) potassium chloride (2.0 g), and the mixture is stirred at room temperature for 20 hours. The precipitated solid is removed by filtration, and the filtrate is concentrated under reduced pressure. To the residue is added water (3 ml), and the resulting crystals are separated by filtration and washed with water and acetone to give cis-dichloro-(3R)-3-aminopyrrolidine platinum (II) (1.28 g) as pale yellow crystal. The physical properties of the cis-dichloro-(3R)-3-aminopyrrolidine platinum (II) thus obtained are identical with those of the cis-dichloro-(3R)-3-aminopyrrolidine platinum (II) as obtained in the above (1-A).

(2) α-Glycolato-(3R)-3-aminopyrrolidine platinum (II) (Isomer a-3):

The above cis-dichloro-(3R)-3-aminopyrrolidine platinum (II) (1.28 g) is suspended in water (15 ml), and to the suspension is added silver sulfate (1.14 g). The mixture is stirred at room temperature for 2 days under light screening, and the insoluble materials are filtered off. To the filtrate is added a 0.5% aqueous potassium chloride solution until no turbidity appears. Excess silver sulfate is precipitated in the form of silver chloride and removed by filtration to give an aqueous solution of cis-sulfato-(3R)-3-aminopyrrolidine platinum (II). To the aqueous solution is added barium hydroxide·8 hydrate (1.15 g), and the mixture is stirred at room temperature for one day. The precipitated barium sulfate and other insoluble materials are removed by filtration to give an aqueous solution of cis-dihydroxo-(3R)-3-aminopyrrolidine platinum (II). To the aqueous solution is added glycolic acid (277 mg), and the mixture is stirred at 60°–70° C. for 3 hours. The reaction mixture is concentrated under reduced pressure, and to the residue is added methanol (20 ml) to give a crude mixture of α-glycolato-(3R)-3-aminopyrrolidine platinum (II) (Isomer a-3) and β-glycolato-(3R)-3-aminopyrrolidine platinum (II) (Isomer a-4). The product is recrystallized from a mixed solvent of methanol-water (10:1) to give α-glycolato-(3R)-3-aminopyrrolidine platinum (II) (Isomer a-3) (508 mg) as colorless crystal. This compound has the following physical properties.

m.p.: It starts to turn gray at around 196° C. and becomes black and is decomposed at around 214° C.

Rf value: about 0.20 [thin layer plate: Kieselgel 60F$_{254}$ (manufacatured by Merck & Co., developer: methanol:water (10:1)]

$[\alpha]_D^{20}$ +11.4° (c=0.5, H$_2$O)

IR (KBr) cm$^{-1}$: 3442, 3116, 2992, 2890, 2816, 1369, 1657, 1347, 1310

SIMS (Secondary ion mass spectrum) m/z: 356 [(M+H)+ based on $^{195}$Pt]

$^1$H-NMR (D$_2$O) α: 1.88–2.07 (2H, m), 2.43 (1H, dd, J=10 Hz, 1 Hz), 3.05 (1H, d, J=10 Hz), 3.18 (1H, d, J=4 Hz), 3.21–3.34 (1H, m), 3.71–3.80 (1H, m), 3.98 (2H, s)

$^{13}$C-NMR (D$_2$O) δ: 30.25, 52.97, 56.68, 62.98, 69.50, 197.06

Elementary analysis for C$_6$H$_{12}$N$_2$O$_3$Pt:
Calcd. (%): C,20.29; H,3.40; N,7.89.
Found (%): C,20.25; H,3.26; N,7.85.

EXAMPLE 4

Preparation of optically active glycolato-3-aminopyrrolidine platinum (II) [α-glycolato-(3S)-3-aminopyrrolidine platinum (II) (Isomer a-5, Platinum complex A-5 of this invention], by Process B:

(1) Cis-dichloro-(3S)-3-aminopyrrolidine platinum (II):

(3S)-3-Aminopyrrolidine L(+)-tartrate (236 mg) prepared in Reference Example 1-(2) is dissolved in water (40 ml) and thereto is added sodium hydroxide (80 mg), and the mixture is stirred at room temperature. To the solution is added platinum (II) potassium chloride (415 mg), and the mixture is stirred at room temperature overnight. The precipitated solid is removed by filtration, and the filtrate is concentrated to dryness under reduced pressure. To the residue is added water (2 ml), and the resulting crystals are separated by filtration and washed with water and acetone to give cis-dichloro- (3S)-3-aminopyrrolidine platinum (II) (221 mg) as pale yellow crystal.

m.p.: It starts to color at around 180° C. and becomes black and is decomposed at 210°-217° C.

$[\alpha]_D^{20} -15.5°$ (c=0.4, H$_2$O)

Elementary analysis for C$_4$H$_{10}$Cl$_2$N$_2$Pt:

Calcd. (%): C,13.64; H,2.86; N,7.96.

Found (%): C,13.58; H,2.58; N,7.95.

(2) α-Glycolato-(3S)-3-aminopyrrolidine platinum (II) (Isomer a-5):

The cis-dichloro-(3S)-3-aminopyrrolidine platinum (II) (6.0 g) obtained in the above method is suspended in water (100 ml), and to the suspension is added silver sulfate (5.31 g). The mixture is stirred at room temperature for 2 days under light screening, and the insoluble materials are filtered off. To the filtrate is added a 0.5% aqueous potassium chloride solution until no turbidity appears. Excess silver sulfate is precipitated in the form of silver chloride and removed by filtration to give an aqueous solution of cis-sulfato-(3S)-3-aminopyrrolidine platinum (II). To the aqueous solution is added barium hydroxide·8 hydrate (5.4 g), and the mixture is stirred at room temperature for one day. The precipitated barium sulfate and other insoluble materials are removed by filtration to give an aqueous solution of cis-dihydroxo(3S)-3-aminopyrrolidine platinum (II). To the aqueous solution is added glycolic acid (1.28 g), and the mixture is stirred at 60°-70° C. for 3 hours. The reaction mixture is concentrated under reduced pressure, and to the residue is added methanol (20 ml) to give a crude mixture of α- glycolato-(3S)-3-aminopyrrolidine platinum (II) (Isomer a-5) and β-glycolato-(3S)-3-aminopyrrolidine platinum (II) (Isomer a-6). This product is recrystallized from a mixed solvent of methanol-water (10:1) to give α-glycolato-(3S)-3-aminopyrrolidine platinum (II) (Isomer a-5) (920 mg) as colorless crystal. This compound has the following physical properties.

m.p.: It starts to color at around 190° C. and becomes black and is decomposed at around 214° C.

Rf value: about 0.20 [thin layer plate: Kieselgel 60F$_{254}$ (manufactured by Merck & Co., developer: methanol-water (10:1)]

$[\alpha]_D^{20} -11.2°$ (c=0.5, H$_2$O)

IR (KBr) cm$^{-1}$: 3442, 3116, 2992, 2890, 2816, 1669, 1657, 1347, 1310

SIMS (Secondary ion mass spectrum) m/z: 356 [(M+H)$^+$ based on $^{195}$Pt]

$^1$H-NMR (D$_2$O) δ: 1.88–2.07 (2H, m), 2.43 (1H, dd, J=10 Hz, 1 Hz), 3.05 (1H, d, J=10 Hz), 3.18 (1H, d, J=4 Hz), 3.21–3.34 (1H, m), 3.71–3.80 (1H, m), 3.98 (2H, s)

$^{13}$C-NMR (D$_2$O) δ: 30.25, 52.97, 56.68, 62.98, 69.50, 197.06

Elementary analysis for C$_6$H$_{12}$N$_2$O$_3$Pt:

Calcd. (%): C,20.29; H,3.40; N,7.89.

Found (%): C,20.29; H,3.25; N,7.93.

EXAMPLE 5

Preparation of glycolato-3-aminopiperidine platinum (II) [a mixture of α-glycolato-(3RS)-3-aminopiperidine platinum (II) (Isomer b-1) and ε-glycolato-(3RS)-3-aminopiperidine platinum (II) (Isomer b-2) in about 6:4 by weight (Platinum complex B-1 of this invention)], by Process A:

(1) Cis-dichloro-(3RS)-3-aminopiperidine platinum (II):

To a solution of (3RS)-3-aminopiperidine (1.7 g) in water (1000 ml) is added platinum (II) potassium chloride (7.2 g) and the mixture is stirred at room temperature for 40 hours. The precipitated solid is removed by filtration, and the filtrate is concentrated under reduced pressure. To the residue is added a small amount of water, and the resulting crystals are separated by filtration and washed with water and acetone to give cis-dichloro-(3RS)-3-aminopiperidine platinum (II) (4.3 g) as pale yellow crystal.

m.p.: It is gradually colored at 165°-180° C. and becomes black and is decomposed at around 215° C.

Elementary analysis for C$_5$H$_{12}$Cl$_2$N$_2$Pt:

Calcd. (%): C,16.40; H,3.30; N,7.65.

Found (%): C,16.35; H,3.25; N,7.61.

(2) Glycolato-3-aminopiperidine platinum (II):

The above cis-dichloro-(3RS)-3-aminopiperidine platinum (II) (4.24 g) is suspended in water (40 ml), and to the suspension is added silver nitrate (3.93 g). The mixture is stirred at room temperature for 2 days under light screening, and the insoluble materials are filtered off. To the filtrate is added a 0.5% aqueous potassium chloride solution until no turbidity appears. Excess silver nitrate is precipitated in the form of silver chloride and removed by filtration to give an aqueous solution of cis-dinitrato-(3RS)-3-aminopiperidine platinum (II). The aqueous solution is passed through a column packed with AMBERLITE ® IRA-400 (manufactured by Rohm and Haas and sold by Organon) (OH type) (70 ml) to give an aqueous solution of cis-dihydroxo-(3RS)-3-aminopiperidine platinum (II). To the aqueous solution is added glycolic acid (880 mg), and the mixture is stirred at 60°-70° C. for 6 hours. The reaction mixture is concentrated under reduced pressure, and the residue is purified by silica gel column chromatography [developer: methanol-water (10:1)]. The eluate is monitored by thin layer chromatography [thin layer plate: Kieselgel 60F$_{254}$, manufactured by Merck & Co., developer: methanol-water (10:1)] and thereby the fractions containing a compound of Rf 0.24 are collected. The solvent is distilled off under reduced pressure, and to the residue is added a small amount of methanol, and the resulting crystals are separated by filtration to give a mixture of stereoisomers of glycolato-3-aminopiperidine platinum (II) (1.33 g) as colorless crystal. It is confirmed by $^1$H-NMR and $^{13}$C-NMR that it is a mixture of α-glycolato-(3RS)-3-aminopiperidine platinum (II) (Isomer b-1) and β-glycolato-(3RS)-3-aminopiperidine platinum (II) (Isomer b-2) (about 6:4 by weight). The isomer mixture has the following physical properties.

m.p.: It is gradually colored at 195°-205° C. and becomes black and is decomposed at around 209° C.

IR (KBr) cm$^{-1}$: 3428, 3144, 3056, 2960, 2920, 2892, 1664, 1344, 1312

SIMS (Secondary ion mass spectrum) m/z: 370 [(M+H)$^+$ based on $^{195}$Pt]

$^1$H-NMR (D$_2$O) δ: 1.56–1.86 (3H, m, peak based on Isomer b-1 and Isomer b-2), 2.52 (0.4H, d, peak based on Isomer b-2), 2.55 (0.6H, d, peak based on Isomer b-1), 2.58–2.76 (1H, m, peak based on Isomer b-1 and Isomer b-2), 2.92–3.38 (4H, m, peak based on Isomer b-1 and Isomer b-2), 4.03 (2H, s, peak based on Isomer b-1 and Isomer b-2)

$^{13}$C-NMR (D$_2$O) δ23.07, 27.79, 54.04, 54.36, 1.78, 197.00 (all of these, six peaks based on Isomer b 1), 69.67 (peak based on Isomer b-1 and Isomer b-2), 23.16, 27.83, 53.13, 54.63, 62.64, 196.92 (all of these, six peaks based on Isomer b-2)

Elementary analysis for C$_7$H$_{14}$N$_2$O$_3$Pt:

Calcd. (%): C,22.77; H,3.82; N,7.59.

Found (%): C,22.71; H,3.66; N,7.48.

EXAMPLE 6

Preparation of glycolato-3-aminopiperidine platinum (II) [α-glycolato-(3RS)-3-aminopiperidine platinum (II) (Isomer b-1, Platinum complex B-2 of this invention], by Process B:

The cis-dichloro-(3RS)-3-aminopiperidine platinum, (II) (842 mg) prepared in the same manner as described in Example 5-(1) is suspended in water (10 ml), and to the suspension is added silver sulfate (717 mg). The mixture is stirred at room temperature for 2 days under light screening, and the insoluble materials are filtered off. To the filtrate is added a 0.5% aqueous potassium chloride solution until no turbidity appears. Excess silver sulfate is precipitated in the form of silver chloride and removed by filtration to give an aqueous solution of cis-sulfato (3RS)-3-aminopiperidine platinum (II). To the aqueous solution is added barium hydroxide·8 hydrate (725 mg), and the mixture is stirred at room temperature for one day. The precipitated barium sulfate and other insoluble materials are removed by filtration to give an aqueous solution of cis-dihydroxo-(3RS)-3-aminopiperidine platinum (II). To the aqueous solution is added glycolic acid (175 mg), and the mixture is stirred at 60°–70° C. for 3 hours. The reaction mixture is concentrated to dryness under reduced pressure, and to the residue is added methanol (10 ml) to give a mixture of α-glycolato-(3RS)-3-aminopiperidine platinum (II) (Isomer b-1) and β-glycolato-(3RS)-3-aminopiperidine platinum (II) (Isomer b-2) (325 mg). The product is recrystallized from a mixed solvent of methanol-water (10:1) to give α-glycolato-(3RS)-3-aminopiperidine platinum (II) (Isomer b-1) (233 mg) as colorless crystal. This compound has the following physical properties.

m.p.: It starts to color at around 211° C. and becomes black and is decomposed at around 223° C.

Rf value: about 0.24 [thin layer plate: Kieselgel 60F$_{254}$ (manufactured by Merck & Co., developer: methanol-water (10:1)]

IR (KBr) cm$^{-1}$: 3448, 3144, 3056, 2964, 2920, 2896, 1664, 1334, 1312

$^1$H-NMR (D$_2$O) δ: 1.56–1.86 (3H, m), 2.55 (1H, d J=11 Hz), 2.70 (1H, td, J=12 Hz, 3 Hz), 2.92–3.48 (4H, m) 4.03 (2H, s)

$^{13}$C-NMR (D$_2$O) δ: 23.07, 27.79, 54.04, 54.36, 61.78, 69.67, 197.00

Elementary analysis for C$_7$H$_{14}$N$_2$O$_3$Pt:
Calcd. (%): C,22.77; H,3.82; N,7.59.
Found (%): C,22.71; H,3.59; N,7.57.

EXAMPLE 7

Preparation of injection preparation

An injection preparation containing as the active ingredient Platinum complex A-1 [a mixture of α-glycolato-(3RS)-3-aminopyrrolidine platinum (II) (Isomer a-1) and β-glycolato-(3RS)-3-aminopyrrolidine platinum (II) (Isomer a-2) in about 1:1 by weight]: [Formulation]

|  | Ratio by weight |
| --- | --- |
| Active ingredient (Platinum complex A-1) | 200 |
| Sodium chloride | 360 |
| Mannitol | 1000 |

[Procedure]

The above components are dissolved in sterilized distilled water (1000 times amount by weight), and the mixture is filtered. The filtrate (each 100 ml) is packed in a vial and lyophilized, and the vial is sealed to give a lyophilized product containing Platinum complex A-1 of this invention in an amount of 100 mg per one vial. This preparation is dissolved in sterilized distilled water (20 ml) when used.

EXAMPLE 8

Preparation of injection preparation

An injection preparation containing as the active ingredient Platinum complex A-2 [α-glycolato-(3RS)-3-aminopyrrolidine platinum (II) (Isomer a-1)]:
[Formulation]

|  | Ratio by weight |
| --- | --- |
| Active ingredient (Platinum complex A-2) | 200 |
| Glucose | 2000 |

[Procedure]

The above components are dissolved in sterilized distilled water (1000 times amount by weight), and the mixture is filtered. The filtrate (each 100 ml) is packed in a vial and lyophilized, and the vial is sealed to give a lyophilized product containing Platinum complex A-2 of this invention in an amount of 100 mg per one vial. This preparation is dissolved in sterilized distilled water (20 ml) when used.

EXAMPLES 9 to 12

Preparation of injection preparation

In the same manner as described in Example 7 except that Platinum complex A-4 [α-glycolato-(3R)-3-aminopyrrolidine platinum (II) (Isomer a-3)], Platinum complex A-5 [α-glycolato-(3S)-3-aminopyrrolidine platinum (II) [Isomer a-5)], Platinum complex B-1 [a mixture of α-glycolato-(3RS-3-aminopiperidine platinum (II) (Isomer b-1) and β-glycolato(3RS)-3-aminopiperidine platinum (II) (Isomer b-2) in about 6:4 by weight], or Platinum complex B-2 [α-glycolato(3RS)-3-aminopiperidine platinum (II) (Isomer b-1)] is used instead of Platinum complex A-1, there are prepared lyophilized products containing Platinum complex A-4, Platinum complex A-5, Platinum complex B-1 or Platinum complex B-2 of this invention in an amount of 100 mg per one vial, respectively.

REFERENCE EXAMPLE 1

Resolution of 3-aminopyrrolidine (1) (3R)-3-Aminopyrrolidine D(−)-tartrate

D(−)-tartaric acid (17 g) is dissolved in a mixture of water (30 ml) and methanol (120 ml), and to the solution is gradually added (3RS)-3-aminopyrrolidine (19 g), and the mixture is stirred. When exothermic reaction is finished, methanol (60 ml) is added to the mixture, and the mixture is allowed to stand at 0°–2° C. overnight. The precipitated crude (3R)-3-aminopyrrolidine D(−)-tartrate (20.6 g) is taken by filtration. This product is recrystallized from a mixture of methanol-water (2:3) four times to give (3R)-3-aminopyrrolidine D(-)-tartrate (6.8 g).

m.p. 219°–227° C.

[α]$_D^{20}$25.9° (c=1, H$_2$O)

Elementary analysis for C$_8$H$_{16}$N$_2$O$_6$:

Calcd. (%): C,40.68; H,6.83; N,11.86.
Found (%): C,40.55; H,6.65; N,11.69.

(2) (3S)-3-Aminopyrrolidine L(+)-tartrate

To the filtrate obtained in the above crude (3R)-3-aminopyrrolidine D(−)-tartrate is added a solution of L(+)-tartaric acid (25 g) in water (50 ml), and the precipitated crystals are separated by filtration. The product is dissolved in a 20% aqueous sodium hydroxide solution (50 ml) and thereto is added acetone (300 ml), and the precipitated crystals are removed by filtration. To the filtrate is added a solution of L(+)-tartaric acid (20 g) in water (40 ml). The precipitated crystals are separated by filtration and dissolved in water (30 ml), and thereto is added sodium hydroxide (300 g). The mixture is extracted with ether (300 ml) three times. Ether is distilled off under reduced pressure, and to the residue is added a solution of L(+)-tartaric acid (5.5 g) in water (25 ml), and the mixture is heated at 80° C. To the mixture is added methanol (40 ml), and the mixture is gradually cooled till room temperature. The precipitated crystals are separated by filtration and recrystallized from a mixed solvent of methanol-water (1:1) to give (3S)-3-aminopyrrolidine L(+)tartrate (5.0 g).
m.p. 219°–226° C.
$[\alpha]_D^{20} +25.9°$ (c=1, H$_2$O)
Elementary analysis for C$_8$H$_{16}$N$_2$O$_6$:
Calcd. (%): C,40.68; H,6.83; N,11.86.
Found (%): C,40.62; H,6.55; N,11.80.

(3) (3R)-3-Aminopyrrolidine

The (3R)-3-aminopyrrolidine D(−)-tartrate (5.0 g). prepared in the above (1) is dissolved in a 40% aqueous sodium hydroxide solution (10 ml), and the mixture is extracted with ether. The extract is dried over anhydrous magnesium sulfate and then distilled to remove ether. The residue is distilled under reduced pressure to give (3R)-3-aminopyrrolidine (0.4 g).
b.p. 70°–72° C./40 mmHg
$[\alpha]_D^{20} +9.0$ (c=1, H$_2$O)

REFERENCE EXAMPLE 2

Preparation of (3S)-3-aminopyrrolidine:
(3S)-3-Amino-2-pyrrolidone hydrochloride (1.5 g) [cf. Beilsteins Handbuch der Organischen Chemie, Drittes und Viertes Erganzungswerk, issued in 1980, page 6401] is suspended in diethyl ether (50 ml), and to the suspension is added lithium aluminum hydride (1.0 g), and the mixture is refluxed with stirring for 48 hours. While stirring under ice cooling, a small amount of ice is added to the reaction mixture to decompose excess lithium aluminum hydride, and the insoluble materials are removed by filtration. The filtrate is dried over anhydrous sodium sulfate, and distilled under reduced pressure to remove diethyl ether. The residue is distilled and fractions of 30°–100° C./25 mmHg are collected to give crude (3S)-3-aminopyrrolidine (216 mg) as an oily substance.
$[\alpha]_D^{20} -6.9°$ (c=1, H$_2$O)

The above crude (3S)-3-aminopyrrolidine is purified in the form of L(+)-tartrate as follows.

The above crude (3S)-3-aminopyrrolidine (200 mg) and L(+)-tartaric acid (348 mg) are dissolved in water (2 ml), and thereto is added methanol (10 ml), and the mixture is allowed to stand at room temperature for one hour to precipitate an oily substance. The superfluid is removed by decantation, and the oily substance is dissolved in a mixed solvent of methanol-water (1:1) with heating, and then the mixture is cooled, and the precipitated impurities are removed by filtration. The filtrate is concentrated to dryness, and the residue is recrystallized from a mixed solvent of methanol-water (2:3) to give (3S)-3-aminopyrrolidine L(+)-tartrate (210 mg).
m.p. 217°–225° C.
$[\alpha]_D^{20} +26.0°$ (c=1, H$_2$O)
Elementary analysis for C$_8$H$_{16}$N$_2$O$_6$:
Calcd. (%): C,40.68; H,6.83; N,11.86.
Found (%): C,40.46; H,6.63; N,22.83.

What is claimed is:

1. A platinum complex of the formula:

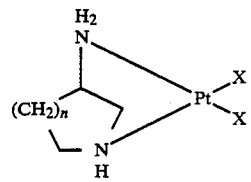

wherein n is an integer of 1 or 2 and X is chlorine, bromine or iodine atom.

* * * * *

UNITED STATES PATENT AND TRADEMARK OFFICE
CERTIFICATE OF CORRECTION

PATENT NO. : 4,968,800
DATED : November 6, 1990
INVENTOR(S) : Masanori TAKAMATSU et al.

It is certified that error appears in the above-identified patent and that said Letters Patent is hereby corrected as shown below:

Column 8, line 14, change "Co$_2$ gas" to --CO$_2$ gas--.

Column 10, Table 4, change "Platinum conplex A-1" to --Platinum complex A-1--.

Column 11, line 20, change "the aqueous" to --To the aqueous--.

Column 12, line 17, change "ar toom" to --at room--.

Column 12, line 27, change "glycolato(3RS)-3" to --glycolato-(3RS)-3--.

Column 12, line 29, change "Isomer a2" to --Isomer a-2--.

Column 12, line 63, change "mainly of" to --mainly composed of--.

Column 12, line 64, change "concentrated to" to --concentrated to dryness--.

Column 14, line 37, change "1369" to --1669--.

Column 15, line 61, change "$\epsilon$-glycolato" to --$\beta$-glycolato--.

Column 16, line 62, change "1.78" to --61.78--.

Column 18, line 41, change "(3RS-3" to --(3RS)-3--.

Column 18, line 67, change "$[\alpha]_D^{20} 25.9$ " to --$[\alpha]_D^{20} -25.9$ --.

Column 20, line 31, change "N,22.83" to --N,11.83--.

Signed and Sealed this

Twenty-third Day of June, 1992

Attest:

DOUGLAS B. COMER

Attesting Officer     Acting Commissioner of Patents and Trademarks